(12) United States Patent
Hacker et al.

(10) Patent No.: US 8,530,386 B2
(45) Date of Patent: *Sep. 10, 2013

(54) HERBICIDAL COMPOSITIONS FOR TOLERANT OR RESISTANT SUGAR BEET CROPS

(75) Inventors: Erwin Hacker, Hochheim (DE);
Hermann Stuebler, Niedernhausen-Oberjosbach (DE);
Hermann Bieringer, Eppstein (DE);
Lothar Willms, Hofheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 469 days.

This patent is subject to a terminal disclaimer.

(21) Appl. No.: 12/182,260

(22) Filed: Jul. 30, 2008

(65) Prior Publication Data
US 2009/0118123 A1 May 7, 2009

Related U.S. Application Data

(62) Division of application No. 10/873,818, filed on Jun. 22, 2004, now Pat. No. 7,422,998, which is a division of application No. 09/762,694, filed as application No. PCT/EP99/05799 on Aug. 10, 1999, now Pat. No. 6,774,085.

(30) Foreign Application Priority Data

Aug. 13, 1998 (DE) .................................. 198 36 673

(51) Int. Cl.
*A01N 43/00* (2006.01)
*A01N 57/00* (2006.01)

(52) U.S. Cl.
USPC ............ 504/128; 504/127; 504/130; 504/139

(58) Field of Classification Search
USPC ................................ 504/128, 127, 130, 139
See application file for complete search history.

(56) References Cited

U.S. PATENT DOCUMENTS 5,990,045 A * 11/1999 Leep et al. .................... 504/128
6,774,085 B1 * 8/2004 Hacker et al. ................. 504/127

* cited by examiner

*Primary Examiner* — Jennifer M Kim
(74) *Attorney, Agent, or Firm* — Frommer Lawrence & Haug LLP

(57) ABSTRACT

Suitable for controlling harmful plants in sugar beet crops composed of tolerant or resistant mutants or transgenic sugar beet plants are herbicide combinations (A)+(B), if appropriate in the presence of safeners, with an effective content of
(A) broad-spectrum herbicides from the group
  (A1) glufosinate (salts) and related compounds,
  (A2) glyphosate (salts) and related compounds such as sulfosate and
  (A3) imidazolinones or their salts
and
(B) herbicides from the group consisting of
  (B0) one or more structurally different herbicides from the abovementioned group (A) or
  (B1) foliar- and predominantly soil-acting herbicides which are active against monocotyledonous and dicotyledonous harmful plants, or
  (B2) herbicides which are active predominantly against dicotyledonous harmful plants, and
  (B3) herbicides which are predominantly foliar-acting and which can be employed against monocotyledonous harmful plants, or
  (B4) herbicides which are both foliar- and soil-acting and which can be employed against monocotyledonous harmful plants,
or of herbicides of more than one of groups (B0) to (B4), the sugar beet crops tolerating the herbicides (A) and (B) present in the combination, if appropriate in the presence of safeners. If appropriate, the combinations are also suitable for regulating the growth or else for controlling the yield or the constituents of sugar beet plants.

17 Claims, No Drawings

HERBICIDAL COMPOSITIONS FOR TOLERANT OR RESISTANT SUGAR BEET CROPS

RELATED APPLICATIONS

This application is a divisional of application U.S. Ser. No. 10/873,818, filed Jun. 22, 2004, now U.S. Pat. No. 7,422,998 and herein incorporated by reference which in turn is a divisional application of 09/762,694, filed Apr. 6, 2001, now issued as U.S. Pat. No. 6,774,085, issued Aug. 10, 2004 and herein incorporated by reference, which in turn is a 371 of PCT/EP99/05799, filed Aug. 10, 1999, which in turn claims priority to German application Ser. No. 198 36 673.6, filed Aug. 13, 1998.

The invention relates to the field of the crop protection products which can be employed against harmful plants in tolerant or resistant crops of sugar beet and which comprise a combination of two or more herbicides as herbicidally active ingredients.

The introduction of tolerant or resistant sugar beet varieties and lines, in particular transgenic sugar beet varieties and lines, leads to the conventional weed control system being complemented by novel active ingredients which are nonselective per se in conventional sugar beet varieties. The active ingredients are, for example, the known broad-spectrum herbicides such as glyphosate, sulfosate; glufosinate, bialophos and imidazolinone herbicides [herbicides (A)], which can now be employed in the tolerant crops developed for each of them. The efficacy level of these herbicides against harmful plants in tolerant crops is high, but, similarly as in the case of other herbicide treatments, depends on the nature of the herbicide employed, the application rate, the formulation in question, the harmful plants to be controlled in each case, the climatic and soil conditions and the like. Furthermore, the herbicides exhibit weaknesses (gaps) with regard to specific harmful plant species. Another criterion is the duration of action or the rate of degradation of the herbicide. Other factors which must be taken into account, if appropriate, are changes in the sensitivity of harmful plants, which may occur localized or upon prolonged use of the herbicides. Losses of action in individual plants can only be compensated for to some extent by increasing the application rates of the herbicides, if at all. Furthermore, there is always a need for methods for achieving the herbicidal action with a lower application rate of active ingredients. Not only does a lower application rate reduce the active ingredient quantity required for application, but, as a rule, it also reduces the quantity of formulation auxiliaries required. Both reduce the economic input and improve the ecological tolerance of the herbicide treatment.

A possibility of improving the use profile of a herbicide can be the combination of the active ingredient with one or more other active ingredients, which contribute the desired additional properties. However, phenomena of physical and biological incompatibility, for example lacking stability of a coformulation, decomposition of an active ingredient or antagonism of the active ingredients, occur not infrequently when using several active ingredients in combination. In contrast, what is desired is combinations of active ingredients with a favorable activity profile, high stability and the greatest degree of synergistically increased action, which allows reduction of the application rate compared with the individual application of the active ingredients to be combined.

Surprisingly, it has now been found that active ingredients from the group of the abovementioned broad-spectrum herbicide (A) in combination with other herbicides from group (A) and, if appropriate, certain herbicides (B) act synergistically in an especially advantageous manner when they are employed in the sugar beet crops which are suitable for the selective use of the first-mentioned herbicides.

Subject-matter of the invention is thus the use of herbicide combinations for controlling harmful plants in sugar beet crops, wherein the herbicide combination in question comprises a synergistically effective content of (A) a broad-spectrum herbicide from the group of the compounds consisting of
(A1) compounds of the formula (A1)

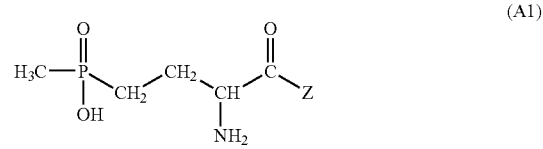

in which Z is a radical of the formula —OH or a peptide residue of the formula —NHCH(CH$_3$)CONHCH(CH$_3$)COOH or —NHCH(CH$_3$)CONHCH[CH$_2$CH(CH$_3$)$_2$]COOH, and its esters and salts, preferably glufosinate and its salts with acids and bases, in particular glufosinate-ammonium, L-glufosinate and its salts, bialaphos and its salts with acids and bases and other phosphinothricin derivatives, (A2) compounds of the formula (A2) and their esters and salts,

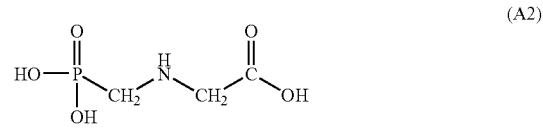

preferably glyphosate and its alkali metal salts and salts with amines, in particular glyphosate-isopropylammonium, and sulfosate, (A3) imidazolinones, preferably imazethapyr, imazapyr, imazamethabenz, imazamethabenzmethyl, imazaquin, imazamox, imazapic (AC 263,222) and their salts, and (B) one or more herbicides from the group of the compounds consisting of
(B0) one or more structurally different herbicides from the abovementioned group (A) and/or
(B1) foliar- and predominantly soil-acting herbicides which are active against monocotyledonous and dicotyledonous harmful plants, preferably from the group consisting of
(B1.1) ethofumesate,
(B1.2) chloridazon,
(B1.3) triflursulfuron and its esters, such as the methyl ester, and
(B1.4) metamitron (PM, pp. 799-801), i.e. 4-amino-4,5-dihydro-3-methyl-6-phenyl-1,2,4-triazin-5-one, and/or
(B2) herbicides which are active predominantly against dicotyledonous harmful plants, for example the compounds
(B2.1) desmedipham,
(B2.2) phenmedipham,
(B2.3) quinmerac and
(B2.4) clopyralid and their salts, and/or (B3) herbicides which are predominantly foliar-acting and which can be employed against monocotyledonous harmful plants, for example the compounds
  (B3.1) quizalofop-P and its esters, if appropriate also in the form of the racemic mixture quizalofop and its esters, preferably quizalofop-P-ethyl or quizalofop-P-tefuryl,
  (B3.2) fenoxaprop-P and its esters, such as the ethyl ester, if appropriate also in the form of the racemic mixture fenoxaprop and its esters, preferably fenoxaprop-P-ethyl,
  (B3.3) fluazifop-P and its esters such as the butyl ester, it appropriate also in the form of the racemic mixture fluazifop and its esters, preferably fluazifop-P-butyl,
  (B3.4) haloxyfop and haloxyfop-P and their esters, such as the methyl or the etotyl ester,
  (B3.5) clodinafop and its esters, in particular the propargyl ester,
  (B3.6) propaquizafop and
  (B3.7) cyhalofop and its salts and esters, and/or
(B4) herbicides which are both foliar- and soil-acting and which can be employed against monocotyledonous harmful plants, for example
  (B4.1) sethoxydim,
  (B4.2) cycloxydim and
  (B4.3) clethodim,
and the sugar beet crops tolerate the herbicides (A) and (B) which are present in the combination, if appropriate in the presence of safeners.

The compounds are referred to by their common names and they are known from the "Pesticide Manual" 11$^{th}$ Ed., British Crop Protection Council 1997 (hereinbelow also abbreviated to "PM"). In addition to the herbicide combinations according to the invention, further crop protection active ingredients and formulation aids and auxiliaries conventionally used in crop protection may be used.

The synergistic effects are observed when the active ingredients (A) and (B) are applied jointly, but can also be observed upon split application (splitting). It is also possible to apply the herbicides or the herbicide combinations in several portions (sequential application), for example after pre-emergence uses, followed by post-emergence applications or after early post-emergence applications, followed by applications at the medium to late post-emergence stage. The simultaneous use of the active ingredients of the combination in question, if appropriate in several portions, is preferred. However, the split application of the individual active ingredients of a combination is also possible and may be advantageous in individual cases. Other crop protection agents such as fungicides, insecticides, acaricides and the like, and/or various auxiliaries, adjuvants and/or fertilizer applications can also be integrated into the use of this system.

The synergistic effects permit reduction of the application rates of the individual active ingredients, a more potent action against the same harmful plant species with the same application rate, the control of species to which the action has previously not extended (gaps), a widened application period and/or a reduced number of the individual applications required, and, as a result for the user, economically and ecologically more advantageous weed control systems.

For example, the combinations of (A)+(B) according to the invention make possible synergistically increased effects which far and unexpectedly exceed the effects which are achieved with the individual active ingredients (A) and (B).

WO-A-98/09525 has already been described a method of controlling weeds in transgenic crops which are resistant to phosphorus-containing herbicides such as glufosinate or glyphosate, where herbicide combinations are employed which comprise glufosinate or glyphosate and at least one herbicide from the group consisting of prosulfuron, primisulfuron, dicamba, pyridate, dimethenamid, metoachlor, flumeturon, propaquizafop, atrazin, clodinafop, norfurazone, ametryn, terbutylazine, simazine, prometryn, NOA-402989 (3-phenyl-4-hydroxy-6-chlorpyridazine), a compound of the formula

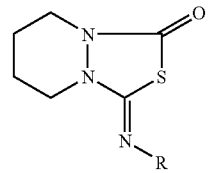

in which R=4-chloro-2-fluoro-5-(methoxycarbonylmethylthio)phenyl (disclosed in U.S. Pat. No. 4,671,819), CGA276854=1-allyloxycarbonyl-1-methylethyl 2-chloro-5-(3-methyl-2,6-dioxo-4-trifluoromethyl-3,6-dihydro-2H-pyrimidin-1-yl)benzoate (=WC9717, disclosed in U.S. Pat. No. 5,183,492) and 4-oxetanyl 2-{N—[N-(4,6-dimethylpyrimidin-2-yl)aminocarbonyl]aminosulfonyl}benzoate (disclosed in EP-A-496701). Details on the effects which can be or have been achieved cannot be found in the publication WO-A-98/09525. Examples of synergistic effects or on carrying out the method in particular crops are absent, as are specific combinations of two, three or further herbicides.

It has been found in our own experiments that, surprisingly, large differences exist between the usability of the herbicide combinations mentioned in WO-A-98/09525 and also other novel herbicide combinations in plant crops.

In accordance with the invention, herbicide combinations are provided which can be employed particularly advantageously in tolerant sugar beet crops.

The compounds of the formulae (A1) to (A4) are known or can be prepared analogously to known methods.

Formula (A1) encompasses all stereoisomers and their mixtures, in particular the racemate and the biologically active enantiomer in each case, for example L-glufosinate and its salts. Examples of active ingredients of the formula (I) are the following.
(A1.1) glufosinate in the narrow sense, i.e. D,L-2-amino-4-[hydroxy(methyl)phosphinyl]butanoic acid,
(A1.2) glufosinate monoammonium salt,
(A1.3) L-glufosinate, L or (2S)-2-amino-4-[hydroxy(methyl)phosphinyl]butanoic acid,
(A1.4) L-glufosinate monoammonium salt,
(A1.5) bialaphos (or bilanofos), i.e. L-2-amino-4-[hydroxy(methyl)phosphinyl]butanoyl-L-alanyl-L-alanine, in particular its sodium salt.

The abovementioned herbicides (A1.1) to (A1.5) are taken up via the green parts of the plants and are known as broad-spectrum herbicides or non selective herbicides; they are inhibitors of the enzyme glutamine synthetase in plants; se "The Pesticide Manual" 11$^{th}$ Edition, British Crop Protection Council 1997, pp. 643-645 and 120-121. While there exists a field of application post-emergence for controlling broad-leaved weeds and grass weeds in plantation crops and on non-crop areas and, using specific application techniques, also for inter-row control in agricultural row crops such as maize, cotton and the like, the importance of the use as selective herbicides in resistant transgenic crops is increasing. Glufosinate is usually employed in the form of salt, preferably of the ammonium salt. The racemate of glufosinate or glufosinate-ammonium alone is usually applied at rates between 200 and 2000 g of A.S./ha (=g of a.i./ha=grams of active substance per hectare). At these rates, glufosinate is effective mainly when taken up via the green parts of the plants. However, since it is degraded microbially in the soil within a few days, it has no long-term action in the soil. This also applies analogously to the related active ingredient bialafos-sodium (also bilanafos-sodium); see "The Pesticide Manual" 11$^{th}$ Ed., British Crop Protection Council 1997, pp. 120-121. As a rule, markedly less active ingredient (A1) is required in the combinations according to the invention, for example an application rate in the range of 20 to 800, preferably 20 to 600, grams of active substance glufosinate per hectare (g of A.S./ha or g of a.i./ha). Corresponding quantities, preferably quantities converted into moles per hectare, also apply to glufosinate-ammonium and bialafos, or bialafos-sodium.

The combinations with the herbicides (A1) which are foliar-acting are expediently employed in sugar beet crops which are resistant to, or tolerate, the compounds (A1). Some tolerant sugar beet crops which have been produced by recombinant technology are already known and are employed in practice; cf. the article in the journal "Zuckerrübe", Vol. 47 (1998), p. 247 et seq.; for the production of transgenic plants which are resistant to glufosinate, cf. EP-A-0242240, EP-A-242236, EP-A-257542, EP-A-275957, EP-A-0513054.

Examples of compound (A2) are
(A2.1) glyphosate, i.e. N-(phosphonomethyl)glycine,
(A2.2) the monoisopropylammonium salt of glyphosate,
(A2.3) the sodium salt of glyphosate,
(A2.4) sulfosate, i.e. the trimesium salt of N-(phosphonomethyl)glycine=the trimethylsulfoxonium salt of N-(phosphono methyl)glycine.

Glyphosate is usually employed in the form of a salt, preferably of the monoisopropylammonium salt or the trimethylsulfoxonium salt (=the trimesium salt=sulfosate). Based on the free amid glyphosate, the individual dose is in the range of 0.5-5 kg of A.S./ha. Glyphosate resembles glufosinate with regard to some application aspects, but is, in contrast to the latter, an inhibitor of the enzyme 5-enolpyruvylshikimate-3-phosphate synthase in plants; see "The Pesticide Manual" 11$^{th}$ Ed., British Crop Protection Council 1997, pp. 646-49. As a rule, application rates in the range of 20 to 1000, preferably 20 to 800, g of A.S./ha glyphosate are required in the combinations according to the invention.

In the case of compounds (A2), too, tolerant plants have been generated by recombinant methods and have been introduced into practice; cf. "Zuckerrübe", year 47 (1998), p. 217 et seq.; cf. also WO 92/00377, EP-A-115673, EP-A-409815.

Examples of imidazolinone herbicide (A3) are
(A3.1) imazapyr and its salts and esters,
(A3.2) imazethapyr and its salts and esters,
(A3.3) imazamethabenz and its salts and esters,
(A3.4) imazamethabenz methyl,
(A3.5) imazamox and its salts and esters,
(A3.6) imazaquin and its salts and esters, for example the ammonium salt,
(A3.7) imazapic (AC 263,222) and its salts and esters, for example the ammonium salt.

The herbicides inhibit the enzyme acetolactate synthase (ALS) and thus protein synthesis in plants; they are both soil- and foliar-acting and some of them exhibit selectivities in crops; cf. "The Pesticide Manual" 11$^{th}$ Ed., British Crop Protection Council 1997 pp. 697-699 for (A3.1), pp. 701-703 for (A3.2), pp. 694-696 for (A3.3) and (A3.4), pp. 696-697 for (A3.5), pp. 699-701 for (A3.6) and pp. 5 and 6, reviewed under AC 263,222 (for A3.7). The application rates of the herbicides are usually between 0.001 and 2 kg of A.S./ha. In the combinations according to the invention, they are in the range of from 10 to 200 g of A.S./ha.

The combinations with imidazolinones are expediently employed in sugar beet crops which are resistant to the imidazolinones. Such tolerant crops are already known. For example, EP-A-0360750 describes the generation of ALS-inhibitor-tolerant plants by selection methods or by recombinant methods. The herbicide tolerance of the plants is generated here by an elevated ALS content in the plants. U.S. Pat. No. 5,198,599 describes sulfonyl urea- and imidazolinone-tolerant plants which have been obtained by selection methods.

Suitable combination partners (B) for component (A) are the compounds of subgroups (B0) to (B4). Specifically, these are:

(B0) herbicides which differ structurally from (which are not identical with) herbicide (A), selected from the group of the herbicides which are possible for component (A), (B1) foliar-acting and predominantly soil-acting herbicides which are active against monocotyledonous and dicotyledonous harmful plants, preferably from the group consisting of (referred to by the common names and the reference in "The Pesticide Manual" 11$^{th}$ Ed., British Crop Protection Council 1997, abbreviated to "PM"):

(B1.1) ethofumesate (PM, pp. 484-486), i.e. 2-ethoxy-2,3-dihydro-3,3-dimethylbenzofuran-5-yl) methanesulfonate, (B1.2) chloridazon (PM, pp. 215-216) i.e. 5-amino-4-chloro-2-phenylpyridazin-3(2H)-one, (B1.3) triflusulfuron and its esters, such as the methyl ester (PM, pp. 1250-1252), i.e. 2-[4-(dimethylamino)-6-(2,2,2-trifluoroethoxy)-1,3,5-triazin-2-yl]carbamoyl-sulfamoyl]-6-methylbenzoic acid and its methyl ester, (B1.4) metamitron (PM, pp. 799-801), i.e. 4-amino-4,5-dihydro-3-methyl-6-phenyl-1,2,4-triazin-5-one, (B2) herbicides which are active predominantly against dicotyledonous harmful plants, for example the compounds (B2.1) desmedipham (PM, pp. 349-350), i.e. phenyl N-[3-(ethoxycarbonylamino)phenyl]carbamate, (B2.2) phenmedipham (PM, pp. 948-949), i.e. 3-methylphenyl N-[3-(methoxycarbonylamino)phenyl]carbamate, (B2.3) quinmerac (PM, pp. 1080-1082), i.e. 7-chloro-3-methylquinoline-8-carboxylic acid, (B2.4) clopyralid (PM, pp. 260-263), i.e. 3,6-dichloropyridine-2-carboxylic acid and its salts, (B3) herbicides which are predominantly foliar-acting and which can be employed against monocotyledonous harmful plants, for example the compounds (B3.1) quizalofop-P and its esters such as the ethyl or tefuryl ester (PM, pp. 1089-1092), i.e. (R)-2-[4-(6-chloroquinoxalin-2-yloxy)phenoxy]propionic acid or its ethyl ester or tetrahydrofufuryl ester, (B3.2) fenoxaprop-P and its esters such as the ethyl ester (PM, pp. 519-520), i.e. (R)-2-[4-(6-chlorobenzoxazol-2-yloxy)phenoxy]-propionic acid and its ethyl ester, (B3.3) fluazifop-P and its esters, such as the butyl ester (PM, pp. 556-557), i.e. (R)-2-[4-(5-trifluoromethylpyridyl-2-yloxy)phenoxy]propionic acid and its butyl ester, (B3.4) haloxyfop and haloxyfop-P and their esters such as the methyl or the etotyl ester (PM, pp. 660-663), i.e. (R,S)- and (R)-2-[4-(3-chloro-5-trifluromethylpyrid-2-yloxy)phenoxy]propionic acid and its methyl ester and etotyl ester, respectively, (B3.5) clodinafop and its esters, in particular the propargyl ester (PM, pp. 251-253), i.e. (R)-2-[4-(5-chloro-3-fluoro-pyridin-2-yloxy)phenoxy]propionic acid and the propargyl ester, (B3.6) propaquizafop (PM, pp. 1021-1022), i.e. isopropylideneaminooxyethyl (R)-2-[4-(6-chloroquinoxatin-2-yloxy)phenoxy]propionate;

(B3.7) cyhalofop and its salts and esters, such as the butyl ester cyhalofop-butyl (PM, pp. 279-1298), i.e. butyl (R)-2-[4-(4-cyano-2-fluorophenoxy)phenoxy]propionate;

(B4) herbicides which are both foliar-acting and soil-acting and which can be employed against monocotyledonous harmful plants, for example (B4.1) sethoxydim (PM, pp. 1101-1103), i.e. (E,Z)-2-(1-ethoxyiminobutyl)-5-[2-(ethylthio)propyl]-3-hydroxycyclohex-2-enone, (B4.2) cycloxydim (PM, pp. 290-291), i.e. 2-(1-ethoxyiminobuytl)-3-hydroxy-5-thian-3-ylcyclohex-2-enone, (B4.3) clethodim (PM, pp. 250-251), i.e. 2-{(E)1-[(E)-3-chlorallyloxy-imino]propyl}-5-[-2(ethylthio)propyl]-3-hydroxycyclohex-2-enone.

The application rates of the herbicides (B) may vary greatly between the individual herbicides. The following ranges are rough indications:

| Compounds (B0): | 5-2000 g A.S./ha (cf. the information on the group of the compounds (A), preferably | |
|---|---|---|
| | glufosinate: | 20-1500 g A.S./ha |
| | glyphosate/sulfosate: | 100-2000 g A.S./ha |
| | imidazolinones: | 5-100 g A.S./ha, |
| Compounds (B1): | 1-5000 g A.S./ha, preferably | |
| | ethofumesate: | 10-3000 g A.S./ha, |
| | chloridazon: | 50-3000 g A.S./ha, |
| | triflursulfuron: | 1-50 g A.S./ha, |
| | metamitron: | 50-5000 g A.S./ha, |
| Compounds (B2): | 5-5000 g A.S./ha, preferably | |
| | desmedipham, phenmedipham; | 10-5000 g A.S./ha, |
| | quinmerac; | 10-1000 g A.S./ha, |
| | clopyralid: | 5-200 g A.S./ha, |
| Compound (B3): | 5-500 g A.S./ha | |
| Compound (B4): | 10-1000 g A.S./ha | |

The quantitative ratios of the compounds (A) and (B) can be seen from the abovementioned application rates of the individual substances and for example, the following quantitative ratios are of particular interest:

(A):(B) in the range from 1000:1 to 1:1000, preferably from 200:1 to 1:100, (A):(B0) preferably from 400:1 to 1:400, in particular 200:1 to 1:200, (A1):(B1) preferably from 1000:1 to 1:250, in particular from 200:1 to 1:50, (A1):(B2) preferably from 300:1 to 1:250, in particular from 100:1 to 1:100, (A1):(B3) preferably from 400:1 to 1:50, in particular from 200:1 to 1:10, (A1):(B4) preferably from 100:1 to 1:50, in particular from 50:1 to 1:20, (A2):(B1) preferably from 2000:1 to 150, in particular from 500:1 to 1:20, (A2):(B2) preferably from 400:1 to 1:50, in particular from 100:1 to 1:20, (A2):(B3) preferably from 500:1 to 1:10, in particular from 200:1 to 1:5, (A2):(B4) preferably from 300:1 to 1:10, in particular from 100:1 to 1:50, (A3):(B1) preferably from 100:1 to 1:500, in particular from 10:1 to 1:100, (A3):(B2) preferably from 20:1 to 1:500, in particular from 10:1 to 1:100, (A3): (B3) preferably from 20:1 to 1:100 in particular from 10:1 to 1:50, (A3):(B4) preferably from 100:1 to 1:200, in particular from 10:1 to 1:50.

The use of the following combinations is of particular interest:

(A1.1)+(B1.1), (A1.1)+(B1.2), (A1.1)+(B1.3), (A1.1)+(B1.4), (A1.2)+(B1.1), (A1.2)+(B1.2), (A1.2)+(B1.3), (A1.2)+(B1.4), (A1.1)+(B2.1), (A1.1)+(B2.2), (A1.1)+(B2.3), (A1.1)+(B2.4), (A1.2)+(B2.1), (A1.2)+(B2.2), (A1.2)+(B2.3), (A1.2)+(B2.4), (A1.1)+(B3.1), (A1.1)+(B3.2), (A1.1)+(B3.3), (A1.1)+(B3.4), (A1.1)+(B3.5), (A1.1)+(B3.6), (A1.1)+(B3.7), (A1.2)+(B3.1), (A1.2)-+(B3.2), (A1.2)+(B3.3), (A1.2)+(B3.4), (A1.2)+(B3.5), (A1.2)+(B3.6), (A1.2)+(B3.7), (A1.1)+(B4.1), (A1.1)+(B4.2), (A1.1)+(B4.3), (A1.2)+(B4.1), (A1.2)+(B4.2), (A1.2)+(B4.3), (A2.2)+(B1.1), (A2.2)+(B1.2), (A2.2)+(B1.3), (A2.2)+(B1.4), (A2.2)+(B2.1), (A2.2)+(B2.2), (A2.2)+(B2.3), (A2.2)+(B2.4), (A2.2)+(B3.1), (A2.2)+(B3.2), (A2.2)+(B3.3), (A2.2)+(B3.4), (A2.2)+(B3.5), (A2.2)+(B3.6), (A2.2)+(B3.7), (A2.2)+(B4.1), (A2.2)+(B4.2), (A2.2)+(B4.3),

The combination of a compound (A) with one or more compounds (B0) is by definition a combination of two or more compounds from group (A). Since the herbicides (A) have a broad activity, such a combination requires that the transgenic plants or mutants show cross resistance to various herbicides (A). Such cross-resistances in transgenic plants have already been disclosed, cf. WO-A-98/20144.

In individual cases, it may be meaningful to combine one or more of the compounds (A) with a plurality of compounds (B), preferably from amongst the classes (B1), (B2), (B3) and (B4).

Furthermore, the combinations according to the invention can be employed together with other active ingredients, for example from the group of the safeners, fungicides, insecticides and plant growth regulators or from the group of the formulation aids and additives conventionally used in crop protection.

Examples of additives are fertilizers and colorants.

Preference is given to herbicide combinations of one or more compounds (A) with one or more compounds of group (B1) or (B2) or (B3) or (B4).

Preference is furthermore given to combinations of one or more compounds (A), for example (A1.2)+(A2.2), preferably of one compound (A), and one or more compounds (B) following the scheme:

(A)+(B1)+(B2), (A)+(B1)+(B3), (A)+(B1)+(B4), (A)+(B2)+(B3), (A)+(B2)+(B4), (A)+(B3)+(B4), (A)+(B1)+(B2)+(B3), (A)+(B1)+(B2)+(B4), (A)+(B1)+(B3)+(B4), (A)+(B2)+(B3)+(B4).

Here, those combinations to which one or more further active ingredients with a different structure [active ingredient (C)] are additionally added, such as (A)+(B1)+(C), (A)+(B2)+(C), (A)+(B3)+(C) or (A)+(B4)+(C), (A)+(B1)+(B2)+(C), (A)+(B1)+(B3)+(C), (A)+(B1)+(B4)+(C), (A)+(B2)+(B4)+(C), or (A)+(B3)+(B4)+(C), are also in accordance with the invention.

The preferred conditions explained hereinbelow in particular for two-way combinations according to the invention primarily also apply to combinations of the last-mentioned type with three or more active ingredients, as long as they comprise the two-way combinations according to the invention, and with regard to the two-way combination according to the invention.

Also of particular interest is the use according to the invention of the combinations of one or more herbicides from group (A), preferably (A1.2) or (A2.2), in particular (A1.2), and one or more herbicides, preferably one herbicide, from the group (B1') ethofumesate, chloridazon, triflursulfuron and metamitron, (B2') desmedipham, phenmedipham, quinmerac and clopyralid, (B3') quizalofop-P, fenoxaprop-P, fluazifop-P, haloxyfop, haloxyfop-P and if appropriate also cyhalofop and (B4') sethoxydim, cycloxydim and clethodim.

Preferred in this context are the combinations of the particular component (A) and one or more herbicides from group (B1'), (B2'), (B3') or (B4').

Furthermore preferred are the combinations (A)+(B1')+(B2'), (A)+(B1')+(B3'), (A)+(B1')+(B4'), (A)+(B2')+(B3'), (A)+(B2')+(B4') or (A)+(B3')+(B4').

The combinations according to the invention (=herbicidal compositions) have an excellent herbicidal activity against a broad range of economically important monocotyledonous and dicotyledonous weeds. The active substances act equally well on perennial weeds which produce shoots from rhizomes, root stocks or other perennial organs and which cannot be easily controlled. In this context, it does not matter whether the substances are applied before sowing, pre-emergence or post-emergence. Preference is given to use post-emergence or early post-sowing pre-emergence.

Some representatives of the monocotyledonous and dicotyledonous weed flora which can be controlled by the compounds according to the invention may be mentioned individually as examples, but this is not to be taken to mean a restriction to certain species.

The monocotyledonous weed species which are controlled well are, for example, *Alopecurus* spp., *Avena* spp., *Setaria* spp., *Echinochloa* spp., *Apera* spp. such as *Apera spica venti*, *Agropyron* spp. and wild forms of cereals, but also *Digitaria* spp., *Lolium* spp., *Phalaris* spp., *Poa* spp., and *Cyperus* species from the annual group, and *Cynodon, Imperata* and *Sorghum* or else perennial *Cyperus* species amongst the perennial species.

In the case of dicotyledonous weed species, the spectrum of action extends to species such as, for example, *chenopodium* spp., *Matricaria* spp., *Kochia* spp., *Veronica* spp., *Viola* spp., *Anthemis* spp., *Polygonum* spp., *Stellaria* spp., *Thiaspi* spp., *Galium* spp., *Amaranthus* spp., *Solanum* spp., *Lanmium* spp., *Cupselia* spp. and *Cirsium* spp., but also *Abutilon* spp., *Chrystanthemum* spp., *Ipomoea* spp., *Pharbitis* spp., *Sida* spp. and *Sinapis* spp., *Convolvulus, Rumex* and *Artemisia*.

If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely.

When the active ingredients are applied post-emergence to the green parts of the plants, growth also stops drastically very soon after the treatment, and the weeds remain at the growth stage of the time of application, or, after a certain period of time, they die completely so that competition by the weeds which is detrimental for the crop plants, is thus eliminated at a very early stage and in a sustained manner.

In comparison with the individual products, the herbicidal compositions according to the invention are distinguished by a herbicidal action which has a faster onset and is more prolonged. As a rule, the rainfastness of the active ingredients of the combinations according to the invention is advantageous. A particular advantage is that the dosages of compounds (A) and (B) which are used in the combinations and which are effective can be set at such a low level that their soil action is optimal. Thus, their use is not only made possible in the first place in sensitive crops, but ground water combinations are virtually avoided. The combination according to the invention of active ingredients makes it possible to reduce the required application rate of the active ingredients considerably.

When herbicides of the type (A)+(B) are applied jointly) superadditive (=synergistic) effects are observed. Here, the action in the combinations exceeds the expected total of the actions of the individual herbicides employed. The synergistic effects permit a reduction in application rate, the control of a broader spectrum of broad-leaved and grass weeds, more rapid onset of the herbicidal action, a prolonged long-term action, better control of the harmful plants with only one, or few, applications, and a widening of the application period which is possible. In some cases, the use of the compositions also reduces the amount of harmful constituents in the crop plant, such as nitrogen or oleic acid.

The abovementioned properties and advantages are required in weed control practice to keep agricultural crops free of undesired competing plants and thus to guarantee the yields in qualitative and quantitative terms, and/or to increase the yields. These novel combinations far exceed the state of the art with regard to the properties described.

Although the compounds according to the invention have an outstanding herbicidal activity against monocotyledonous and dicotyledonous weeds, the tolerant, or cross-tolerant, sugar beet plants only suffer negligible damage, if any.

In addition, some of the compositions according to the invention have outstanding growth-regulatory properties in the sugar beet plants. They engage in the plants' metabolism in a regulatory manner and can therefore be employed for the targeted control of plant constituents. Moreover, they are also suitable for generally regulating and inhibiting undesired vegetative growth without killing the plants in the process.

Owing to their herbicidal and plant-growth-regulatory properties, the compositions can be employed for controlling harmful plants in known tolerant or cross-tolerant sugar beet crops or in tolerant or genetically modified sugar beet crops which are yet to be developed. As a rule, the transgenic plants are distinguished by particularly advantageous properties, for example in addition to the resistances to the compositions according to the invention by resistances to fungal diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased oil content or whose quality has been modified, for example the fatty acid spectrum of the harvested material is different.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

- recombinant modifications of crop plants for the purposes of modifying the starch synthesized in the plants (for example WO 92/11376, WO 92/14827, WO 91/19806),
- transgenic crop plants which exhibit resistances to other herbicides, for example to sulfonylureas (EP-A-0257993, U.S. Pat. No. 5,013,659),
- transgenic crop plants with the ability of producing *Bacillus thuringiensis* toxins (Bt toxins), which make the plants resistant to certain pests (EP-A-0142924, EP-A-0193259),
- transgenic crop plants with a modified fatty acid spectrum (WO 91/13972),
- transgenic sugar beet with resistance to herbicides of the acetolactate synthase inhibitor type, such as imidazolinones (WO-A-98/02526, WO-A-98/02527, WO-A-98/2562).

A large number of techniques in molecular biology, with the aid of which novel transgenic plants with modified properties can be generated, are known in principle; see, for example, Sambrook et al., 1989, Molecular Cloning, A Laboratory Manual, $2^{nd}$ Ed., Cold Spring Harbor Laboratory Press, Cold Spring Harbor, N.Y.; or Winnacker "Gene und Klone" [Genes and Clones], VCH Weinheim $2^{nd}$ Edition 1996 or Christou, "Trends in Plant Science" 1 (1996) 423-431).

To carry out such recombinant manipulations, nucleic acid molecules can be introduced into plasmids which permit a mutagenesis or a sequence alteration, by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves trans-scripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants can be plants of any desired plant species, i.e. both monocotyledonous and dicotyledonous plants.

Thus, transgenic plants can be obtained which exhibit modified properties owing to the overexpression, suppression or inhibition of homologous (=natural) genes or gene sequences or expressing heterologous (=foreign) genes or gene sequences.

A subject matter of the invention is therefore also a method of controlling undesired vegetation in tolerant sugar beet crops, which comprises applying one or more herbicides of type (A) together with one or more herbicides of type (B) to the harmful plants, organs thereof or the area under cultivation.

Subject-matter of the invention are also the novel combinations of compounds (A)+(B) and herbicidal compositions comprising them.

The active ingredient combinations according to the invention can both exist as mixed formulations of the two components, if appropriate together with further active ingredients, additives and/or customary formulation auxiliaries, which are then applied in the customary manner as a dilution with water, and be produced as so-called tank mixes by jointly diluting the separately formulated, or partially separately formulated, components with water.

The compounds (A) and (B) or their combinations can be formulated in various ways, depending on the prevailing biological and/or chemico-physical parameters. Examples of general formulation possibilities which are suitable are: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing materials, granules for soil application or spreading, or water-dispersible granules (WG), ULV formulations, microcapsules or waxes.

The individual formulation types are known in principle and are described, for example, in: Winnacker-Küchler, "Chemische Technologie" [Chemical Engineering], Volume 7, C. Hauser Verlag Munich, $4^{th}$ Ed. 1986; van Valkenburg, "Pesticides Formulations", Marcel Dekker N.Y., 1973; K. Martens, "Spray Drying Handbook", $3^{rd}$ Ed. 1979, G. Goodwin Ltd. London.

The necessary formulation auxiliaries, such as inert materials, surfactants, solvents and further additives, are also known and are described, for example, in: Watkins, "Handbook of Insecticide Dust Diluents and Carriers", $2^{nd}$ Ed., Darland Books, Caldwell N.J.; H. v. Olphen, "Introduction to Clay Colloid Chemistry"; $2^{nd}$ Ed., J. Wiley & Sons, N.Y. Marsden, "Solvents Guide", $2^{nd}$ Ed., Interscience, N.Y. 1950, McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesellschaft, Stuttgart 1976, Winnacker-Küchler, "Chemische Technologie", Volume 7, C. Hauser Verlag Munich, $4^{th}$ Ed. 1986.

Based on these formulations, it is also possible to prepare combinations with other pesticidally active substances, such as other herbicides, fungicides or insecticides, and with safeners, fertilizers and/or growth regulators, for example in the form of a ready mix or a tank mix.

Wettable powders (sprayable powders) are products which are uniformly dispersible in water and which, besides a diluent or inert material, additionally comprise ionic or nonionic surfactants (wetters, dispersants), for example polyethoxylated alkylphenols, polyethoxylated fatty alcohols or fatty amines, alkanesulfonates or alkylbenzenesulfonates, sodium lignosulfonate, sodium 2,2'-dinaphthylmethane-6,6-disulphonate, sodium dibutylnaphthalenesulfonate, or else sodium oleoylmethyltauride.

Emulsifiable concentrates are prepared by dissolving the active ingredient in an organic solvent, for example butanol, cyclohexanone, dimethylformamide, xylene, or else higher-boiling aromatics or hydrocarbons with addition of one or more ionic or nonionic surfactants (emulsifiers). Examples of emulsifiers which can be used are: calcium alkylarylsulfonates such as calcium dodecylbenzenesulfonate or nonionic emulsifiers such as fatty acid polyglycol esters, alkylaryl polyglycol ethers, fatty alcohol polyglycol ethers, propylene oxide/ethylene oxide condensates, alkyl polyethers, sorbitan tatty acid esters, polyoxyethylene sorbitan fatty acid esters or polyoxyethylene sorbitol esters.

Dusts are obtained by grinding the active ingredient with finely divided solid materials, for example talc, natural clays such as kaolin, bentonite and pyrophyllite, or diatomaceous earth.

Granules can be prepared either by spraying the active ingredient onto adsorptive, granulated inert material or by applying active ingredient concentrates by means of binders, for example polyvinyl alcohol, sodium polyacrylate or else mineral oils, to the surface of carriers such as sand, kaolinites or of granulated inert material. Also, suitable active ingredients may be granulated in the manner customary for the preparation of fertilizer granules, if desired as a mixture with fertilizers. Water-dispersible granules are, as a rule, prepared by methods such as spray drying, fluidized-bed granulation, disk granulation, mixing with high-speed mixers and extrusion without solid inert material.

As a rule, the agrochemical preparations comprise 0.1 to 99 percent by weight, in particular 2 to 95% by weight, of active ingredients of types A and/or B, the following concentration being customary, depending on the formulation type:

In wettable powders, the active ingredient concentration is, for example, approximately 10 to 95% by weight, the remainder to 100% being composed of customary formulation components. In the case of emulsifiable concentrates, the active ingredient concentration can amount to, for example, 5 to 80% by weight.

Formulations in the form of dusts usually comprise 5 to 20% by weight of active ingredient, sprayable solutions approximately 0.2 to 25% by weight of active ingredient.

In the case of granules, such as dispersible granules, the active ingredient content depends partly on whether the active ingredient is in liquid or solid form and on which granulation auxiliaries and fillers are being used. As a rule, the content in the case of the water-dispersible granules ranges between 10 and 90% by weight.

In addition, the abovementioned active ingredient formulations comprise, if appropriate, the binders, wetters, dispersants, emulsifiers, preservatives, antifreeze agents, solvents, fillers, colorants, carriers, antifoams, evaporation inhibitors, pH regulators or viscosity regulators which are conventional in each case.

For example, it is known to improve the action of glufosinate-ammonium (A1.2) and that of its L-enantiomer by surface-active substances, preferably by wetters from the series of the alkyl polyglycol ether sulfates which contain, for example, 10 to 18 carbon atoms and which are used in the form of their alkali metal or ammonium salts, but also as the magnesium salt, such as sodium $C_{12}/C_{14}$ fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227-232 (1988). Furthermore, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are, if appropriate, diluted in the customary manner, for example using water in the case of wettable powders, emulsifiable concentrates, dispersions and water-dispersible granules. Preparations in the form of dusts, soil granules, granules for spreading and sprayable solutions are usually not diluted further with other inert materials prior to use.

The active ingredients can be applied to the plants, plant organs, plant seeds or the area under cultivation (soil of a field), preferably to the green plants and plant organs and, if appropriate, additionally to the soil of the field. One possibility of using the active ingredients is their joint application in the form of tank mixes, where the optimally formulated concentrated formulations of the individual active ingredients are mixed jointly in the tank with water, and the resulting spray mixture is applied.

A joint herbicidal formulation of the combination according to the invention of (A) and (B) has the advantage that it is easier to apply since the amounts of the components are preset in the correct ratio to each other. Also, the auxiliaries in the formulation can be matched optimally to each other, while a tank mix of different formulations may lead to undesired combinations of auxiliaries.

A. GENERAL FORMULATION EXAMPLES a) A dust is obtained by mixing 10 parts by weight of an active ingredient/active ingredient mixture and 90 parts by weight of talc as inert substance and comminuting the mixture in a hammer mill,
b) A wettable powder which is readily dispersible in water is obtained by mixing 25 parts by weight of an active ingredient/active ingredient mixture, 64 parts by weight of kaolin-containing quartz as inert substance, 10 parts by weight of potassium lignosulfonate and 1 part by weight of sodium oleoylmethyltauride as wetter and dispersant and grinding the mixture in a pinned-disc mill.
c) A dispersion concentrate which is readily dispersible in water is obtained by mixing 20 parts by weight of an active ingredient/active ingredient mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277° C.) and grinding the mixture in a bowl mill to a fineness of below 5 microns.
d) An emulsifiable concentrate is obtained from 15 parts by weight of an active ingredient/active ingredient mixture, 75 parts by weight of cyclohexanone as solvent and 10 parts by weight of oxethylated nonylphenol as emulsifier.
e) Granules which are dispersible in water are obtained by mixing
75 parts by weight of an active ingredient/active ingredient mixture,
10 parts by weight of calcium lignosulfonate,
5 parts by weight of sodium lauryl sulfate
3 parts by weight of polyvinyl alcohol and
7 parts by weight of kaolin,
grinding the mixture in a pinned-disc mill and granulating the powder in a fluidized bed by spraying on water as granulation liquid,
f) Water-dispersible granules are also obtained by homogenizing and precomminuting, on a colloid mill,
25 parts by weight of an active ingredient/active ingredient mixture,
5 parts by weight of sodium 2,2'-dinaphthylmethane-6,6'-disulfonate,
2 parts by weight of sodium oleoylmethyltauride, 1 part by weight of polyvinyl alcohol,
17 parts by weight of calcium carbonate and
50 parts by weight of water,
subsequently grinding the mixture in a bead milt and atomizing and drying the resulting suspension in a spray tower by means of a single-substance nozzle.

BIOLOGICAL EXAMPLES

1. Pre-Emergence Action on Weeds

Seeds or rhizome pieces of monocotyledonous and dicotyledonous harmful plants are placed in sandy loam in cardboard pots and covered with soil. The compositions, which are formulated in the form of concentrated aqueous solutions, wettable powders or emulsion concentrates, are then applied to the surface of the covering soil at various dosages as aqueous solution, suspension or emulsion at an application rate of 600 to 800 l of water per ha (converted). After the treatment, the pots are placed in the greenhouse and kept under good growth conditions for the weeds. Visual scoring of the plant damage or the adverse effect on emergence was done after the test plants had emerged after an experimental period of 3 to 4 weeks in comparison with untreated controls. As shown by the test results, the compositions according to the invention have a good herbicidal pre-emergence activity against a broad spectrum of grass weeds and broad-leaved weeds.

In this context, activities of the combinations according to the invention are frequently observed which exceed the formal total of the activities when the herbicides are applied individually (=synergistic effect).

If already the observed activity values exceed the formal total of the values in the experiments with individual application, then they also exceed Colby's expected value, which is calculated by the following formula and which is also regarded as indicating synergism (cf. S. R. Colby, in Weeds 15 (1067) pp. 20 to 22):

$$E=A+B-(A\cdot B/100)$$

In this formula, A, B indicate the activity of the active ingredients A and B in % at a and b g A.S./ha, respectively, and E indicates the expected value in % at a+b g A.S./ha.

At suitable low dosages, the observed experimental values show an effect of the combinations which exceeds Colby's expected values.

2. Post-Emergence Action on Weeds

Seeds or rhizomes of monocotyledonous and dicotyledonous weeds are placed in sandy loam soil in cardboard pots, covered with soil and grown in the greenhouse under good growth conditions. Three weeks after sowing, the experimental plants are treated at the three-leaf stage with the compositions according to the invention. The compositions according to the invention, which are formulated as wettable powders or as emulsion concentrates, are sprayed at various dosages onto the green plant organs at an application rate of 600 to 800 l of water per ha (converted). After the experimental plants have remained in the greenhouse for approx. 3 to 4 weeks under optimal growth conditions, the effect of the preparations is scored visually in comparison with untreated controls. The compositions according to the invention also have a good herbicidal activity against a broad spectrum of economically important grass weeds and broad-leaved weeds when applied post-emergence.

In this context, activities of the combinations according to the invention are frequently observed which exceed the formal total of the activities when the herbicides are applied individually. The observed values show, at suitably low dosages, an activity of the combinations which exceed Colby's expected values (cf. scoring in Example 1).

3. Herbicidal Action and Crop Plant Tolerance

Field Trial

Transgenic sugar beet plants with resistance to one or more herbicides (A) were grown together with typical weed plants in the open in 2×5 m plots under natural field conditions; alternatively, the weed population established naturally while the sugar beet plants grew. Treatment with the compositions according to the invention and, for control purposes, with separate application of the active ingredients of the components alone, was carried out under standard conditions with a plot sprayer at an application rate of 200-300 liters of water per hectare in parallel trials in accordance with the scheme of Table 1, i.e. pre-sowing/pre-emergence, post-sowing/pre-emergence or post-emergence at the early, medium or late stage.

TABLE 1

| Use scheme - Examples | | | | |
|---|---|---|---|---|
| Application of the active ingredients | Pre-emergence | Post-emergence up to the 2-leaf stage | Post-emergence 2-4-leaf stage | Post-emergence 6-leaf stage |
| combined | (A3.2) + (A3.5) | | | |
| " | (A3.2) + (B1.4) | | | |
| " | (B2.3) + (B1.4) | | | |
| " | | (A) + (B) | | |
| " | | | (A) + (B) | |
| " | | | | (A) + (B) |
| sequential | (A3) | (A1) | | |
| " | (B1.1) | (A2.2) | | |
| " | (B1.1) | | (A2.2) | |
| " | | (A2.2) | (B2.2) | |
| " | | (B2.2) | (A2.2) | |
| " | | (B2.2) | | (A2.2) |
| " | | (A2.2) | | (B2.2) |
| " | | (A2.2) + (B2.2) | | |
| " | | | (A2.2) + (B2.2) | |
| " | | | | (A2.2) + (B2.2) |
| " | | (A) | (A') | |
| " | (A) | (B) | | |
| " | | (B) | (A) | |
| " | | | (B) | (A) |

TABLE 1-continued Use scheme - Examples

| Application of the active ingredients | Pre-emergence | Post-emergence up to the 2-leaf stage | Post-emergence 2-4-leaf stage | Post-emergence 6-leaf stage |
|---|---|---|---|---|
| " | | (A) | (B) | |
| " | | (A) | (B) | |
| " | | (A) + (B) | (A) + (B) | |
| " | | (A) | | (A) + (B) |
| " | | | | (A2.2) + (B2.2) |
| " | | | (A) + (B) | (B) |
| " | (A) + (B) | (A) + (B) | | |
| " | | (A) + (B) | (A) + (B) | |
| " | | (A) + (B) | (A) + (B) | (A) + (B) |

Abbreviations in Table 1:
(B1.4) = metamitron
(B2.3) = quinmerac
(B1.1) = ethofumesate
(B3.2) = fenoxaprop-P-ethyl
(A2.2) = glyphosate-isopropylammonium
(B2.2) = phenmedipham
(A) or (B) or (A1) or (A3) = all possible herbicides of type (A) or (B) or (A1) or (A3) as defined in the description.

At 2, 4, 6 and 8 week intervals after application, the herbicidal activity of the active ingredients or active ingredient mixtures were scored visually by comparing the treated plots with untreated control plots. Damage and development of all aerial plant organs was recorded. The scoring was done using a percentage scale (100% activity=all plants dead, 50% activity=50% of the plants and green plant organs dead, 0% activity=no discernible effect=like control plot). The score values of in each case 4 plots were averaged.

The comparison demonstrated that the combinations according to the invention usually exhibit a greater, in some cases considerably greater, herbicidal activity than the total of the actions of the individual herbicides (=$E^a$). In important sections of the score period, the activities exceeded Colby's expected values (=$E^c$) (cf. score in Example 1) and therefore suggest that synergism is present. In contrast, the sugar beet plants suffered no, or only negligible, damage as a consequence of the treatment with the herbicidal compositions.

TABLE 2

Herbicidal action in sugar beet - field trial

| Active ingredient(s) | Dose[1] g A.S./ha | Herbicidal action[2] in % against *Setaria viridis* | Damage to transgenic sugar beet |
|---|---|---|---|
| (A1.2) | 300 | 98 | 0 |
| | 150 | 95 | 0 |
| | 75 | 85 | 0 |
| | 37.5 | 35 | 0 |
| (B1.3) | 17 | 20 | 0 |
| | 8 | 0 | 0 |
| (A1.2) + (B1.3) | 37.5 + 8 | 55 ($E^a$ = 35) | 0 |
| | 75 + 8 | 90 ($E^a$ = 85) | 0 |

Abbreviations for Table 2:
[1] = application in 2-4-leaf stage
[2] = scoring 3 weeks after application
(A1.2) = glufosinate-ammonium
(B1.3) = trisulfuron-methyl
Also see the generally used abbreviations hereinbelow:
Generally used abbreviations for the tables:
g A.S./ha = gram active substance (100% active ingredient) per hectare
$E^a$ = formal total of the individual herbicidal activities
$E^c$ = Colby's expected value (cf. scoring In Example 1)
"transgenic sugar beet" = sugar beet which, owing to a resistance gene, tolerates the respective active ingredient (A).

TABLE 3

Herbicidal action in sugar beet crop (greenhouse experiment)

| Active ingredient(s) | Dose[1] g A.S./ha | Herbicidal action[2] in % against *Galium aparine* | Damage to transgenic sugar beet |
|---|---|---|---|
| (A1.2) | 500 | 85 | 0 |
| | 250 | 60 | 0 |
| | 125 | 45 | 0 |
| (B2.2) | 2000 | 30 | 0 |
| | 1000 | 30 | 0 |
| | 500 | 20 | 0 |
| (B1.4) | 3000 | 5 | 0 |
| | 1500 | 5 | 0 |
| | 750 | 5 | 0 |
| (B2.4) | 200 | 45 | 0 |
| | 100 | 35 | 0 |
| | 50 | 5 | 0 |
| (A1.2) + (B2.2) | 500 + 500 | 96 ($E^c$ = 88) | 0 |
| | 250 + 500 | 85 ($E^a$ = 80) | 0 |
| | 125 + 2000 | 81 ($E^a$ = 75) | 0 |
| (A1.2) + (B1.4) | 500 + 750 | 95 ($E^a$ = 90) | 0 |
| (A1.2) + (B2.4) | 500 + 50 | 93 ($E^a$ = 90) | 0 |
| | 125 + 200 | 92 ($E^a$ = 90) | 0 |

Abbreviations for Table 3: see after Table 2, plus additionally
[1] = application in the 4-5-leaf stage
[2] = scoring 3 weeks after application
(A1.2) = glufosinate-ammonium
(B1.4) = metamitron
(B2.2) = phenmedipham
(B2.4) = clopyralid

TABLE 4

Herbicidal action and selectivity in sugar beet crop (field trial)

| Active ingredient(s) | Dose[1] g A.S./ha | Herbicidal action[2] in % against *Echinochloa crus-galli* | Damage to transgenic sugar beet |
|---|---|---|---|
| (A1.2) | 65 | 85 | 0 |
| | 10 | 60 | 0 |
| | 0 | 45 | 0 |
| (B4.1) | 315 | 85 | 0 |
| | 210 | 73 | 0 |
| | 105 | 35 | 0 |

TABLE 4-continued

Herbicidal action and selectivity in sugar beet crop (field trial)

| Active ingredient(s) | Dose[1] g A.S./ha | Herbicidal action[2] in % against *Echinochloa crus-galli* | Damage to transgenic sugar beet |
|---|---|---|---|
| (B4.2) | 250 | 93 | 0 |
|  | 125 | 70 | 0 |
|  | 62.5 | 45 | 0 |
| (A1.2) + (B4.1) | 350 + 210 | 88 ($E^a$ = 83) | 0 |
|  | 175 + 210 | 78 ($E^a$ = 73) | 0 |
|  | 350 + 105 | 75 ($E^a$ = 45) | 0 |
| (A1.2) + (B4.2) | 350 + 62.5 | 96 ($E^c$ = 55) | 0 |
|  | 175 + 250 | 95 ($E^a$ = 93) | 0 |

Abbreviations for Table 4: see after Table 2, plus additionally
[1] = application in 3-leaf stage
[2] = scoring 4 weeks after application
(A1.2) = glufosinate-ammonium
(B4.1) = sethoxydim
(B4.2) = cycloxydim

TABLE 5

Herbicidal action and selectivity in sugar beet crop (field trial)

| Active ingredient(s) | Dose[1] g A.S./ha | Herbicidal action[2] in % against *Avena fatua* | Damage to transgenic sugar beet |
|---|---|---|---|
| (A1.2) | 600 | 95 | 0 |
|  | 300 | 65 | 0 |
|  | 150 | 30 | 0 |
| (B3.2) | 60 | 85 | 0 |
|  | 30 | 60 | 0 |
|  | 15 | 20 | 0 |
| (B3.4) | 30 | 63 | 0 |
|  | 15 | 20 | 0 |
| (A1.2) + (B3.2) | 300 + 15 | 93 ($E^a$ = 85) | 0 |
|  | 150 + 15 | 75 ($E^a$ = 50) | 0 |
| (A1.2) + (B3.4) | 300 + 15 | 96 ($E^c$ = 85) | 0 |
|  | 150 + 30 | 95 ($E^a$ = 93) | 0 |

Abbreviations for Table 5: see after Table 2, plus additionally
[1] = application in the 3-5-leaf stage
[2] = scoring 4 weeks after application
(A1.2) = glufosinate-ammonium
(B3.2) = fenoxaprop-ethyl (rac.)
(B3.4) = haloxyfop-P-methyl

TABLE 6

Herbicidal action (field trial)

| Active ingredient(s) | Dose[1] g A.S./ha | Herbicidal action[2] in % against *Galium aparine* | Herbicidal action[2] in % against *Kochia scoparia* |
|---|---|---|---|
| (A1.2) | 600 | 85 | 75 |
|  | 300 | 40 | 52 |
|  | 250 | 20 | 30 |
| (B) | 413 | 30 | 0 |
| (B1.1 + 2.1 + 2.2) | (256 + 32 + 125) |  |  |
| (A1.2) + (B) | 300 + 413 | 88 ($E^a$ = 70) | 75 ($E^a$ = 52) |

Abbreviations for Table 6: see after Table 2, plus additionally
[1] = application in the 3-5-leaf stage
[2] = scoring 4 weeks after application
(A1.2) = glufosinate-ammonium
(B) = coformulation of (B1.1) + (B2.1) + (B2.2)
(B1.1) = ethofumesate
(B2.1) = desmedipham
(B2.2) = phenmedipham

TABLE 7

Herbicidal action (field trial)

| Active ingredient(s) | Dose[1] g A.S./ha | Herbicidal action[2] in % against *Galium aparine* |
|---|---|---|
| (A2.2) | 1000 | 85 |
|  | 500 | 60 |
|  | 250 | 40 |
|  | 125 | 10 |
| (B2.2) | 2000 | 30 |
|  | 1000 | 30 |
|  | 500 | 20 |
| (B) | 413 | 30 |
| (B1.1 + 2.1 + 2.2) | (256 + 32 + 125) |  |
| (A2.2) + (B2.2) | 500 + 500 | 85 ($E^a$ = 80) |
|  | 500 + 2000 | 93 ($E^a$ = 90) |
| (A2.2) + (B) | 500 + 413 | 95 ($E^a$ = 90) |
|  | 125 + 413 | 75 ($E^a$ = 40) |

Abbreviations for Table 7: see after Table 2, plus additionally
[1] = application in the 4-5-leaf stage
[2] = scoring 26 days after application
(A2.2) = glyphosate-isopropylammonium
(B) = coformulation of (B1.1) + (B2.1) + (B2.2)
(B1.1) = ethofumesate
(B2.1) = desmedipham
(B2.2) = phenmedipham

TABLE 8

Herbicidal action (field trial)

| Active ingredient(s) | Dose[1] g A.S./ha | Herbicidal action[2] in % against *Amaranthus retroflexus* | Herbicidal action[2] in % against *Setaria viridis* |
|---|---|---|---|
| (B1.4)[3] | 3500 | 73 | 20 |
| (A.1.2)[4] | 200 | 55 | 60 |
| [(B2.3) + (B1.2)][5] | 250 + 2000 | 72 | — |
| (B1.4)[3] + (A.1.2)[4] | 3500 + 200 | 98 ($E^c$ = 88) | 95 ($E^a$ = 80) |

TABLE 8-continued

Herbicidal action (field trial)

| Active ingredient(s) | Dose[1] g A.S./ha | Herbicidal action[2] in % against *Amaranthus retroflexus* | Herbicidal action[2] in % against *Setaria viridis* |
| --- | --- | --- | --- |
| [B2.3) + (B1.2)][5] + (A1.2)[4] | (250 + 2000) +200 | 96 (E$^c$ = 87) | — |

Abbreviations for Table 6: see after Table 2, plus additionally
[1] = sequential treatment, specific application depending on the active ingredient, i.e.
[3] = and
[5] = in each case pre-emergence and
[4] = post-emergence at the 2-3-leaf stage
[2] = scoring 22 days after application
(A1.2) = glufosinate-ammonium
(B1.4) = metamitron
(B2.3) + (B1.2) = quinmerac + chloridazon, coformulated

The invention claimed is:

1. A method for controlling harmful plants in sugar beet crops which comprises:
   applying to the crops, seeds, plants, plant organs, or area under cultivation a synergistically effective amount of a combination of:
   (A) a broad-spectrum herbicide is selected from the group of the compounds consisting of:
      (A1) compounds of the formula (A1), and their esters and salts:

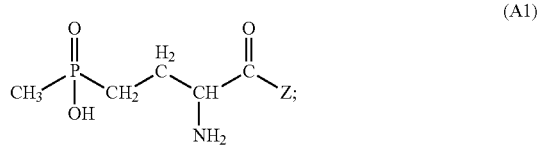

(A1)

in which Z is a radical of the formula —OH or a peptide residue of the formula —NHCH(CH$_3$)CONHCH(CH$_3$)COOH or —NHCH(CH$_3$)CONHCH[CH$_2$CH(CH$_3$)$_2$]COOH; and
   (A2) compounds of the formula (A2) and their esters and salts:

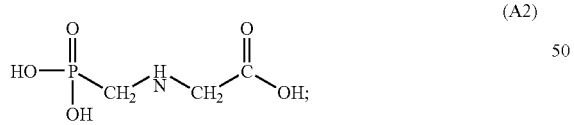

(A2)

and combinations thereof;
(B) one or more herbicides selected from the group of the compounds consisting of:
   B1') ethofumesate, chloridazon, triflusulfuron and esters thereof, and metamitron;
   B2') desmedipham, phenmedipham, quinmerac, clopyralid, and the salts of these compounds;
   B3') quizalofop-P, fenoxaprop-P, fluazifop-P, haloxyfop, haloxy-P, and cyhalofop, and the salts and esters of these compounds; and
   B4') sethoxydim, cycloxydim, and clethodim; and
optionally, additives and/or formulation aids conventionally used in crop protection.

2. The method as claimed in claim 1;
   wherein the broad-spectrum herbicide is a compound of the formula (A2) or their esters or salts.
3. The method as claimed in claim 2;
   wherein the compound of the formula (A2) is glyphosate-isopropyl-ammonium.
4. The method as claimed in claim 3;
   wherein one or more herbicides (B) is selected from the group consisting of:
      B1) ethofumesate and triflusulfuron, and esters thereof;
      B2) desmedipham, phenmedipham, quinmerac, and the salts of these compounds;
      B3) haloxyfop, haloxyfop-P, cyhalofop, and the salts and esters of the last-mentioned three compounds; and
      B4) cycloxydim.
5. The method of as claimed in claim 4;
   wherein the one or more herbicides (B) is ethofumesate.
6. The method as claimed in claim 4;
   wherein the one or more herbicides (B) is triflusulfuron.
7. The method as claimed in claim 2;
   wherein one or more herbicides (B) is selected from the group consisting of:
      B1) chloridazon and metamitron;
      B2) clopyralid and the salts of this compound;
      B3) quizalofop-P, fenoxaprop-P, fluazifop-P, and the salts and esters of these compounds; and
      B4) sethoxydim and clethodim.
8. A method of controlling harmful plants in tolerant sugar beet crops, which comprises:
   applying a synergistically effective amount of the herbicides or herbicide combination of:
   (A) a broad-spectrum herbicide is selected from the group of the compounds consisting of:
      (A1) compounds of the formula (A1), and their esters and salts:

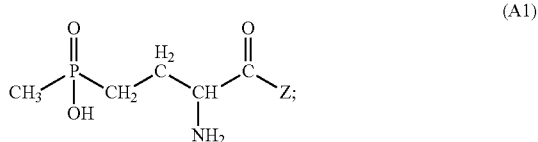

(A1)

in which Z is a radical of the formula —OH or a peptide residue of the formula —NHCH(CH$_3$)CONHCH(CH$_3$)COOH or —NHCH(CH$_3$)CONHCH[CH$_2$CH(CH$_3$)$_2$]COOH; and
   (A2) compounds of the formula (A2) and their esters and salts:

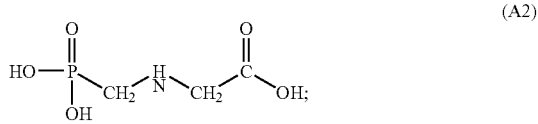

(A2)

and combinations thereof;
(B) one or more herbicides selected from the group of the compounds consisting of:
   B1') ethofumesate, chloridazon, triflusulfuron and esters thereof, and metamitron;
   B2') desmedipham, phenmedipham, quinmerac, clopyralid, and the salts of these compounds;

B3') quizaiofop-P, fenoxaprop-P, fluazifop-P, haloxyfop, haloxy-P, and cyhalofop, and the salts and esters of these compounds; and B4') sethoxydim, cycloxydim, and clethodim; and optionally, additives and/or formulation aids conventionally used in crop protection;

wherein the herbicides (A) and (B) are applied jointly or separately, pre-emergence, post-emergence, or pre- and post-emergence to the plants, plant organs, plant seeds, or the area under cultivation.

9. The method as claimed in claim 8;
wherein the broad-spectrum herbicide is a compound of the formula (A1) or their esters or salts.

10. The method as claimed in claim 9;
wherein the compound of the formula (A1) is glufosinate-ammonium.

11. The method as claimed in claim 8;
wherein the broad-spectrum herbicide (A) is a compound of the formula (A2) or their esters or salts.

12. The method as claimed in claim 11;
wherein the compound of the formula (A2) is glyphosate-isopropylammonium.

13. The method as claimed in claim 8;
wherein a herbicide combination of one or more herbicides (A) and ethofumesate (herbicide (B)) is first applied jointly and then one or more herbicides (A) are applied.

14. The method as claimed in claim 13;
wherein a herbicide combination of a herbicide (A1) or (A2) and ethofumesate (herbicide (B)) is first applied jointly and then a herbicide (A2) or (A1) is applied.

15. The method as claimed in claim 8;
wherein one or more herbicides (A) are applied firstly and then a combination of one or more herbicides (A) and ethofumesate (herbicide (B)) is applied.

16. The method as claimed in claim 15;
wherein a herbicide combination of a herbicide (A1) or (A2) and ethofumesate (herbicide (B)) is first applied jointly and then a herbicide (A2) or (A1) is applied.

17. The method of as claimed in claim 8;
wherein a herbicide combination of triflusulfuron or ester thereof (herbicide (B)) and ethofumesate (herbicide (B)) is applied after separately applying one or more herbicides (A).

* * * * *